(12) United States Patent
Meyer (10) Patent No.: US 6,325,625 B1
(45) Date of Patent: Dec. 4, 2001

(54) DENTAL SEPARATOR AND MATRIX STABILIZING DEVICE

(75) Inventor: Alvin Meyer, San Mateo, CA (US)

(73) Assignee: Dentsply International Inc.

( * ) Notice: Subject to any disclaimer, the term of this patent is extended or adjusted under 35 U.S.C. 154(b) by 0 days.

(21) Appl. No.: 09/577,436

(22) Filed: May 22, 2000

Related U.S. Application Data (63) Continuation-in-part of application No. 09/340,761, filed on Jun. 28, 1999.

(51) Int. Cl.[7] .............................. A61C 5/12; A61C 5/00; A61C 5/04; A61C 9/00
(52) U.S. Cl. .................... 433/139; 433/140; 433/39; 433/40
(58) Field of Search .................... 433/139, 140, 433/138, 137, 39, 37, 34, 40

(56) References Cited

U.S. PATENT DOCUMENTS

| | | | | |
|---|---|---|---|---|
| 1,031,533 | * | 7/1912 | Davidson | 433/139 |
| 1,336,746 | | 4/1920 | Ivory | 433/139 |
| 2,507,938 | | 5/1950 | Smith | 433/139 |
| 2,706,333 | | 4/1955 | Schultz | 433/139 |
| 4,004,345 | | 1/1977 | Ely | 433/139 |
| 4,265,623 | | 5/1981 | Soelberg et al. | 433/136 |
| 4,373,915 | | 2/1983 | Comstock | 433/136 |
| 4,601,662 | | 7/1986 | Galler | 433/136 |
| 4,639,221 | | 1/1987 | Sairenji | 433/136 |
| 4,661,063 | | 4/1987 | Levy | 433/136 |
| 4,718,852 | | 1/1988 | Galler | 433/136 |
| 4,787,849 | | 11/1988 | Jacoby et al. | 433/136 |
| 5,199,869 | | 4/1993 | McGann | 433/21 |
| 5,314,331 | | 5/1994 | Brosius et al. | 433/21 |
| 5,503,556 | | 4/1996 | Leonard et al. | 433/136 |
| 5,607,302 | | 3/1997 | Garrison et al. | 433/39 |
| 5,975,906 | | 11/1999 | Knutson | 433/226 |

FOREIGN PATENT DOCUMENTS

656387 * 5/1929 (FR) ...................... 433/139

* cited by examiner

*Primary Examiner*—John J. Wilson
*Assistant Examiner*—Robyn Kieu Doan
(74) *Attorney, Agent, or Firm*—James B. Bieber (57) ABSTRACT

A dental separator and matrix stabilizing device (40) for applying pressure against adjacent teeth (68, 70) to temporarily force the teeth apart from one another for dental and orthodontic procedures. The device (40) includes a spring yoke (42), opposing tines (46), and engagement structures (44). The opposing tines (46) are adapted for wedging between interdental surfaces of the adjacent teeth (68, 70). The engagement structures (44) are adapted for receiving a spreading instrument (58). The opposing tines (46) engage the profile of a tooth along a zone of contact. The device is adapted be used in combination with a plurality of like devices (40, 40').

18 Claims, 6 Drawing Sheets

DENTAL SEPARATOR AND MATRIX STABILIZING DEVICE

RELATED APPLICATIONS

This application is a Continuation-in-Part of U.S. patent application Ser. No. 09/340,761 filed Jun. 28, 1999, entitled Dental Spring with Engagement Apertures, the full disclosure of which is incorporated herein by reference.

BACKGROUND OF THE INVENTION

1. Field of Invention

This invention relates to dental implements, specifically to a dental separator for applying pressures against adjacent teeth to force the teeth apart from one another. In particular, this invention relates to temporary dental implements for enlarging the space between adjacent teeth as necessary for various dental procedures such as dental restorative treatments and applying dental matrices, dental matrix shims and orthodontic bands. The invention also relates to a dental implement which may, in addition to forcing adjacent teeth apart, be used to stabilize dental matrices.

2. Description of Related Art

When tooth decay occurs in a zone proximal an abutting tooth, thin bands or shims, commonly known as dental "matrices", are wrapped around the tooth being treated. The matrix provides a temporary form which will hold fluid restorative material in a controlled shape until the restorative material cures. Thin bands are also wrapped around teeth in order to grasp and reposition teeth relative to neighboring teeth of a dental arch for orthodontic treatments. Space to accommodate the thickness of such bands and shims between abutting teeth must be generated by mechanically forcing the abutting teeth apart.

It is well known that treating a tooth without separating it from its abutment tooth may create an unnatural and troublesome configuration between the treated tooth and the abutment tooth causing a pathologic response from the surrounding tissues. In the interest of providing healthful services, dentists must recreate firm tooth-to-tooth contact as is natural in dental arches and important to dental health. To accomplish appropriate contact, the involved teeth must be forced apart temporarily to create a sufficient space for the thickness of a dental matrix and to allow proper shaping of restorative material as it cures.

Once a dental matrix is positioned between involved teeth, the matrix must be stabilized to allow the dentist to manipulate its contours without dislodging it. For example, some restorative materials, notably silver amalgam alloys, must be scrubbed into a prepared void of the treated tooth with force, thus requiring rigid stabilization of the dental matrix to resist disfigurement of its contours during such scrubbing in order to prevent resulting disfigurement of the treated tooth.

Various devices have been used to spread adjacent teeth, most commonly, a wedge of wood or plastic is forced into the interdental or proximal space. Such wedges forced into the triangular void between teeth disadvantageously develop a vertical force vector as well as the intended horizontal separating force vector. The undesirable vertical force vector often traumatizes the gum tissue at the base of the triangular void.

U.S. Pat. Nos. 4,601,662 and 4,718,852 to Galler are directed to a screw impelled vise forcing elements between and against teeth. This device disadvantageously loses its spreading influence after the teeth yield to a first pressure increment and thus requires sequential increments to extend the separating influence. The Galler device is inserted into the triangular void or interproximal triangle between teeth and disadvantageously creates undesirable vertical force vectors. As the elements are forced into the interproximal triangle, the device vertically presses against and traumatizes soft gum tissues at the base of the interproximal triangle.

U.S. Pat. No. 1,336,746 to Ivory discloses a rubber dam clamp which engages a single tooth along lingual and buccal surfaces of the tooth. The Ivory device does not contact interdental surfaces between abutting teeth and will not provide a separation force between abutting teeth.

Similar to the Ivory device, U.S. Pat. Nos. 2,706,333 to Schultz, 4,004,345 to Ely, 4,265,623 to Soelberg et al, 4,639,221 to Sairenji, 4,661,063 to Levy, and 4,787,849 to Jacoby et al. each disclose a device which engages a single tooth along lingual and buccal surfaces of the tooth. Similarly, these devices do not contact interdental surfaces between abutting teeth and do not provide a separation force between abutting teeth.

U.S. Pat. No. 5,503,556 to Leonard et al. discloses a device which extends along abutting teeth, however, the interior arcuate surface of the Leonard device engages along lingual and buccal surfaces of a single tooth instead of interdental surfaces between abutting teeth. Thus, the Leonard device does not provide a separation force between abutting teeth.

U.S. Pat. No. 5,199,869 to McGann and U.S. Pat. No. 5,314,331 to Broslus et al. each disclose orthodontic wire springs placed between adjacent teeth perpendicular to the occlusal plane with wires extending into and occupying the proximal space between the adjacent teeth. Although the McGann and Broslus devices apply a tooth spacing force on adjacent teeth during orthodontic treatment, such devices are not conducive to restorative dental procedures because the wire springs occupy the very work space required for such dental procedures.

U.S. Pat. No. 5,607,302 to Garrison discloses an apparatus for retaining a dental matrix against a tooth. The disclosed matrix retainer apparatus is not designed to separate adjacent teeth. Instead, Garrison discloses discrete wedges, which are used in combination with the matrix retainer apparatus, to separate adjacent teeth.

U.S. Pat. No. 4,373,915 to Comstock discloses an iatrogenic shield having sufficient elasticity to deform for placement against a tooth to be protected wherein its side walls contract against the buccal and lingual surfaces of the tooth. The Comstock device is sufficiently thin to pass between the interproximal surfaces of adjacent teeth, however the device is not designed to generate a force for separating adjacent teeth.

U.S. Pat. 5,975,906 to Knutson discloses a soft polymer dental strip similar to PTFE thread seal tape commonly found in plumbing stores. The dental strip is an over-wrap designed to cover freshly applied restorative material until the material is cured.

Circular spring clips have been known to the dental profession as teeth separating devices. They were engaged by spreading forceps at two mid-points across the diameter of a circular yoke. As such spring clips are stretched, distention is limited to the proximal half of the yoke whereby the distal half does not contribute to the spring bias of the clip. A disadvantage of such known spring clips is that distention is limited to the proximal half of the yoke which may cause permanent distortion of the device and a loss of effectiveness. Another disadvantage is that teats of a spreading tool engage such known spring clips at lateral surfaces of the circular yoke thus creating an axis about which the device may rock resulting in increased difficulty in exact placement of the device against teeth.

SUMMARY OF THE INVENTION

In summary, the present invention is directed to a dental separator and matrix stabilizing device for applying pressure against adjacent teeth to force the teeth apart from one another for various dental and orthodontic procedures. The dental separator and matrix stabilizing device of the present invention includes a spring yoke, a pair of opposing tines, and a pair of engagement structures. The opposing tines are adapted for wedging between interdental surfaces of the adjacent teeth. The opposing tines are biased toward one another along a closure path. Engagement of the tines with interdental surfaces of the adjacent teeth generates a force vector substantially perpendicular to the closure path thereby forcing the adjacent teeth apart. The device of the present invention may also be used to properly position dental matrices in contact against the surface of a treated tooth.

It is an object of the present invention to provide a dental separator and matrix stabilizing device for use in combination with conventional rubber-dam clamp-spreading forceps to enlarge the interdental spaces between abutting teeth.

It is another object of the present invention to provide a dental separator and matrix stabilizing device that minimizes vertical force vectors generated by the device in order to minimize discomfort and trauma to surrounding tissue of a patient.

It is another object of the present invention to provide a dental separator and matrix stabilizing device that minimizes obstructions in a dentist's field of view of a dental treatment site.

It is another object of the present invention to provide a dental separator and matrix stabilizing device that is configured to position a spring yoke of the device away from a dentist's work space during a restorative dental procedure.

It is yet another object of the present invention to provide a dental separator and matrix stabilizing device simultaneously usable in combination with like devices.

The accompanying drawings, which are incorporated in and form a part of this specification, illustrate embodiments of the invention and, together with the description, serve to explain the principles of the invention.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
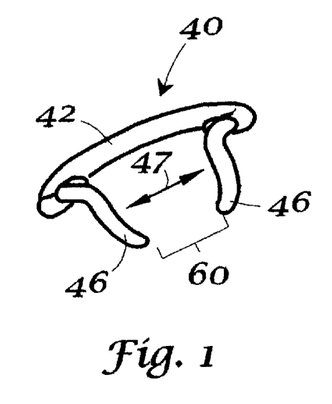
FIG. 1 is an isometric view of a dental separator and matrix stabilizing device in accordance with the present invention.

Turning now to the drawings, wherein like components are designated by like reference numerals throughout the various figures, FIG. 1 shows a dental separator and matrix stabilizer device in accordance with the present invention. In particular, a dental separator and matrix stabilizer device 40 includes a yoke 42, a pair of engagement structures 44, and a pair of opposing tines 46. When engagement structures 44 are spread apart by a dentist using a spreading instrument such as forceps, the resiliency of yoke 42 biases opposing tines 46 toward one another along a closure path, as indicated by arrow 47 in FIG. 1. When dental separator 40 is positioned on a dental arch such that opposing tines 46 contact the angular interdental surfaces of abutting teeth, the inward biasing of the resilient yoke 42 causes tines 46 to wedge in between the abutting teeth and exert a force on the interdental surfaces oriented generally perpendicular to the closure path thereby forcing the abutting teeth apart.

Figure 2:
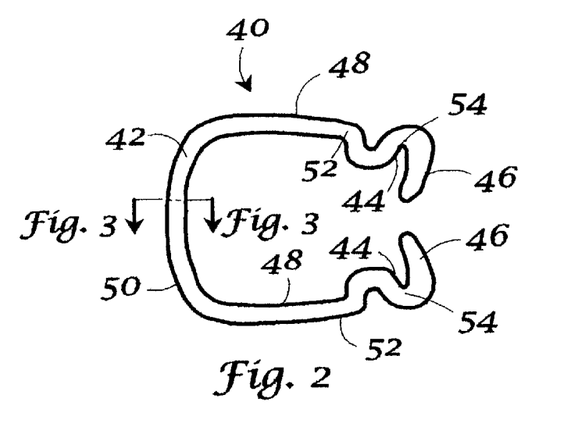
FIG. 2 is a plan view of the dental separator and matrix stabilizing device shown in FIG. 1.
Figure 4:
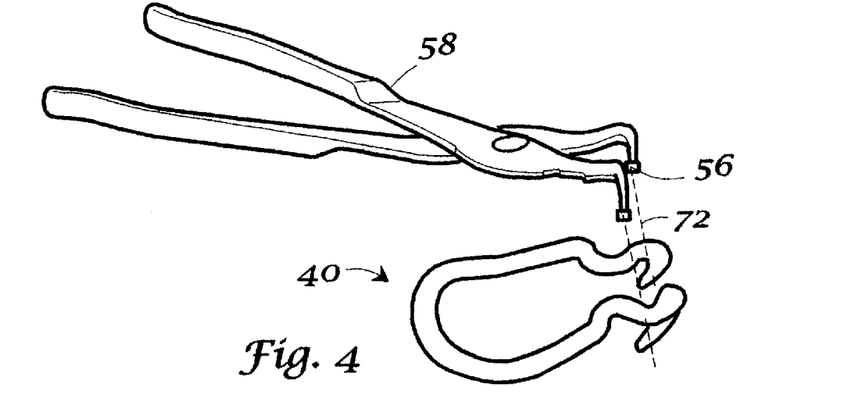
FIG. 4 is an isometric view of the dental separator and matrix stabilizing device of FIG. 1 shown in use with a spreading tool in position to engage engagement structures of the device.

Yoke 42 includes a pair of longitudinal segments 48 interconnected by a transverse segment 50, which are generally coplanar with one another. Each longitudinal segment 48 terminates in a respective yoke end 52 distal from transverse segment 50. A pair of engagement structures or receptacles 44 are provided adjacent each yoke end 52. One should appreciate, however, that the engagement structures may take the form of protrusions instead of receptacles. Engagement receptacles 44 in the form of invaginations 54 provide an engagement surface for receiving a pair of teats 56 of rubber-dam clamp-spreading forceps 58, as shown in FIG. 4. Yoke 42 and engagement receptacles 44 are generally coplanar. A tine 46 extends downwardly from each of engagement receptacles 44. Each tine 46 is spaced from the other by a distance as indicated by tine-to-tine gap 60 in FIG. 1. The length of gap 60 is generally less than the width of teeth involved in a dental procedure. Preferably, as shown in FIGS. 1 and 2, dental separator 40 is bilaterally symmetrical.

Yoke 42, receptacles 44 and tines 46 are integrally, and most preferably monolithically, formed of a firm resilient material. Preferably, dental separator 40 is formed of stainless steel, such as American Iron and Steel formulas 302 and/or 304. One should appreciate that other alloys or plastics may be used, such as nickel-titanium alloy, nickel or plated spring steel, and American Iron and Steel formula 420.

Figure 3A:
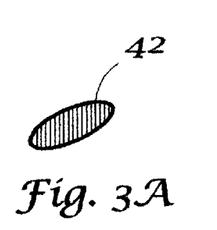
FIGS. 3A–3D a cross-sectional view of the dental separator and matrix stabilizing device shown in FIG. 1 taken along line 3—3 in FIG. 2 and three alternative embodiments thereof.
Figure 3B:
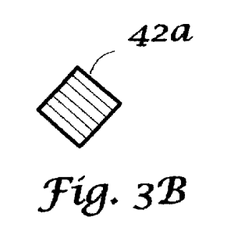
Figure 3C:
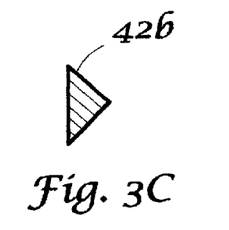
Figure 3D:
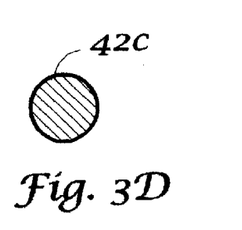

Preferably, the outer dimensions of dental separator 40 are approximately 1.0" by 0.75". Such outer dimensions provide sufficient open space between longitudinal segments 48 to provide a dentist with an unobstructed view of and access to a treated tooth. Preferably, the cross-sectional dimensions of dental separator 40 are approximately 1.0–2.5 mm. Such cross-sectional dimensions provide the device with sufficient resiliency without unnecessary bulk which would impede a dentist's field of view. One should appreciate, however, that the actual dimensions may vary depending upon the intended patient and the degree of resiliency desired. The cross-sectional shape of dental separator 40 shown in FIGS. 1 and 2 is elliptical, as is shown in FIG. 3A. FIGS. 3B–3D show alternative shapes which may be used, including rectangular, triangular, and circular cross-sectional shapes. One should appreciate that other suitable cross-sectional shapes may be used, however, the cross-sectional shape preferably has rounded corners to ensure proper contact with the interdental surfaces of the involved teeth, to minimize discomfort of the patient, and to minimize damage to surrounding tissue.

Figure 5:
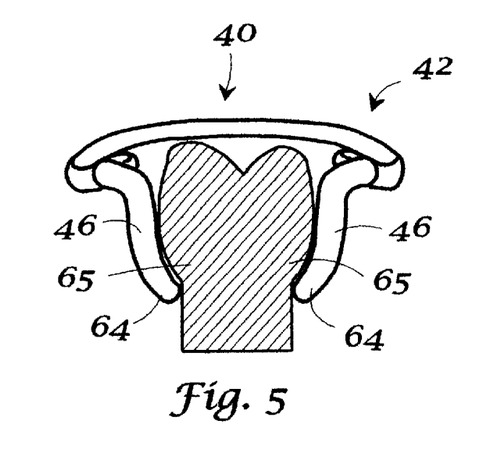
FIG. 5 is a sectional view of a tooth with the dental separator and matrix stabilizing device of FIG. 1 opened by a spreading tool (not shown) and poised to engage the tooth.
Figure 6:
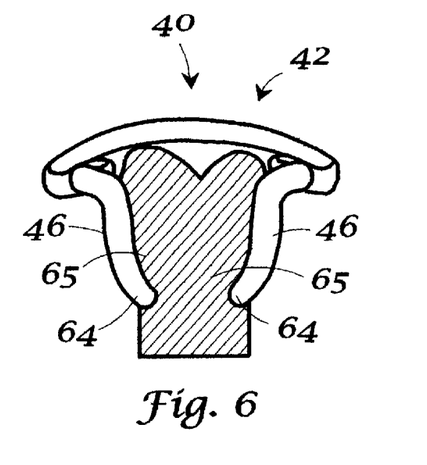
FIG. 6 is a sectional view of a tooth with the dental separator and matrix stabilizing device of FIG. 1 released to allow the tines to spring into engagement with the tooth.

As shown in FIGS. 5 and 6, opposing tines 46 converge toward one another and have a concave profile shaped to follow a normal tooth profile and engage interproximal involutions of adjacent teeth extending toward the gingiva. In particular, terminal portions 64 of tines 46 arc or curl toward one another following natural curvatures of adjacent teeth thus creating a vertically extending zone of contact. In particular, terminal portions follow the curvature of the undercut segment 65 of a tooth adjacent its root connection whereby the zone of contact extends along a length of tines 46.

Figure 7:
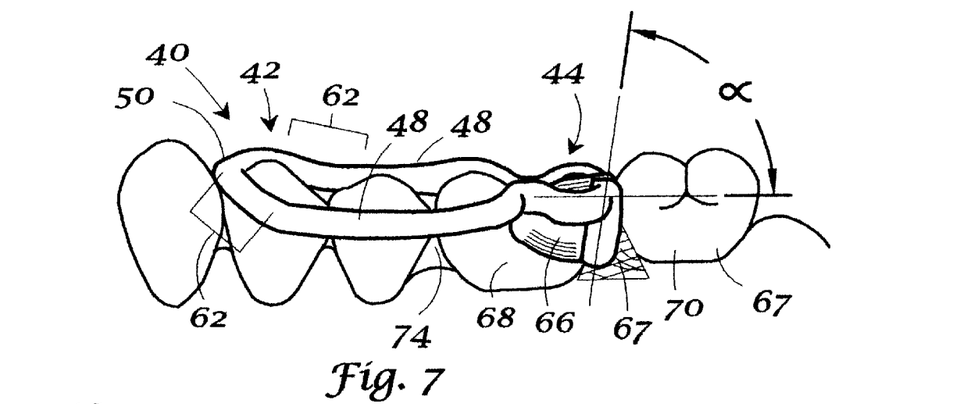
FIG. 7 is a lateral view of the dental separator and matrix stabilizing device of FIG. 1 shown in use with a typical dental matrix application on a dental arch.

As shown in FIG. 7, yoke 42 and engagement receptacles 44 are generally coplanar. Each tine 46 extends from a receptacle 44 at an acute angle a with respect to the yoke plane, that is the plane in which yoke 42 and receptacles 44 generally extend. Preferably, each tine extends from a respective receptacle at an angle of approximately 70–90°, and preferably between 80–90°, with respect to the yoke plane. The relative angle of the tines to the yoke facilitates positioning the yoke and receptacles generally within, or parallel to, the occlusal plane of the patient. Such positioning is beneficial because it further minimizes obstructions of a dentist's field of view of a treated tooth. Yoke 42 is also provided with declining extensions 62 along a portion of longitudinal segments 48 proximal transverse segment 50. Declining extensions 62 allow the bulk of dental separator 40 to be positioned slightly lower than the occlusal plane further enhancing a dentist's field of view.

Generally, the dental separator of the present invention is used in combination with conventional rubber-dam clamp-spreading forceps to position the dental separator on a patient's dental arch in order to enlarge the spaces between abutting teeth and/or to stabilize a dental matrix during a dental restorative or orthodontic procedure.

Dental restorative procedures and orthodontic procedures often require additional interproximal space between a treatment tooth, the tooth upon which restorative treatment such as a filling is performed, and a neighboring or adjacent tooth. For example, additional interproximal space is generally necessary to insert a contoured dental matrix 66 and to compensate for the thickness of a temporary matrix shim used as a form. Alternatively, interproximal space may be required for positioning orthodontic bands between adjacent teeth (not shown).

Tooth drift may require further spacing to adjust for any drifting of adjacent teeth which may have occurred during an extended decay period. For example, it is often necessary to reestablish the proper arch length which often diminishes during the decay period, as is the case when decay destroys tooth tissue at points of abutment and the adjacent teeth migrate together to close the resulting gap between the teeth.

Referring to FIG. 4, an operator will use a pair of rubber-dam clamp-spreading forceps 58, a common instrument in dental armamentaria, to grip and manipulate dental separator 40. In particular, an operator will insert teats 56 along a substantially vertically oriented insert trajectory 72 into engagement receptacles 44 of dental separator 40. Thus engaged, the operator may selectively squeeze spreading forceps 58 to move tines 46 toward and away from each other along closure path 47 (FIG. 1). The operator must exert a degree of pressure on the forceps in order to overcome the biasing force of yoke 42.

The operator may also use the spreading forceps 58 to excessively spread tines 46 apart from one another or to pinch tines 46 together in order to adjust the degree of spring tension of yoke 42 by way of deformation of the yoke. For example, excessively forcing tines 46 apart from one another so as to deform yoke 42 increases the tine-to-tine gap 60 and correspondingly decreases the spring tension of the yoke 42. Similarly, excessively pinching tines 46 toward one another so as to deform yoke 42 decreases the tine-to-tine gap 60 and correspondingly increases the spring tension of the yoke 42.

Once the spring tension of dental separator 40 is properly adjusted, or if no adjustment is necessary, the dentist will grasp dental separator 40 with spreading forceps 58 and squeeze forceps 58 to sufficiently open tines 46 enough to clear the width of the involved teeth of a dental arch 67. Using spreading forceps 58, the dentist will position the dental separator 40 such that tines 46 are adjacent interproximal surfaces 69, 71 of a treated tooth 68 and an abutting tooth 70, as shown in FIGS. 6 and 7. Treated tooth 68 and abutting tooth 70 are collectively referred to as the involved teeth 68, 70.

Once the operator releases pressure on forceps 58, the biasing force of yoke 42 draws tines 46 toward one another to provide a wedging effect on the interdental surfaces 69, 71 (FIG. 10) of the involved teeth 68, 70. The angular relationship of the interdental surfaces of adjacent teeth generally forms a triangular or pyramidal invagination whereby the closing force generated between tines 46 along closure path 47 will be diverted into a force perpendicular to the closure path 47 and substantially parallel to the patient's occlusal plane. The resulting perpendicular force against the adjacent involved teeth 68, 70 causes the involved teeth to move apart from one another thereby increasing the interproximal space between them. Such space provides workspace for a dentist to perform the desired dental procedure.

As noted above, tines 46 are formed to follow the normal profile of a tooth, whereby tines 46 contact the interproximal surfaces of the involved teeth 68, 70 along a substantial length of tines 46 as shown in FIG. 6. The perpendicular separating force exerted on the involved teeth is distributed along a zone of contact of tines 46 against the interdental surfaces which vertically extends along a vertical length of the interdental surfaces of the involved teeth 68, 70. Undesirable vertical forces are minimized, thus minimizing discomfort and possible trauma to the gingival embrasure 74 which is often occluded by soft tissue of the gingiva or gums.

Also, because tines 46 engage the involved teeth along a zone of contact instead of a point, dental separator 40 is less likely to create a moment arm which may cause the involved teeth to pivot about their respective roots.

Figure 8:
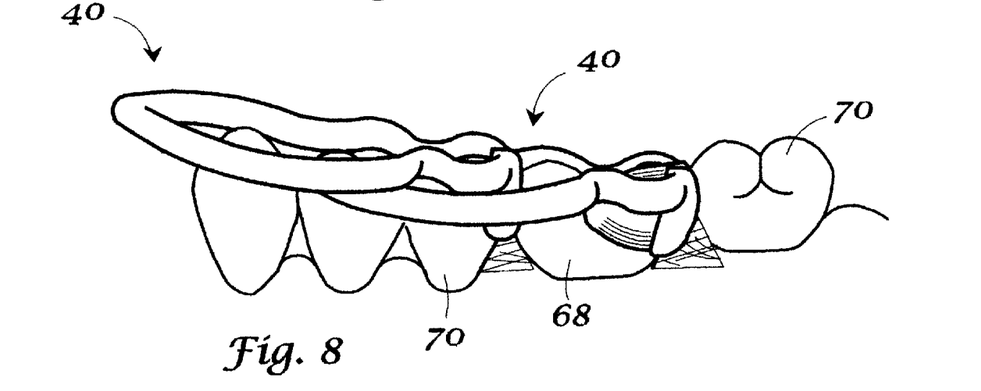
FIG. 8 is a lateral view of the dental separator and matrix stabilizing device of FIG. 1 in use with a second dental separator and matrix stabilizing device.

Referring to FIG. 8, one should appreciate that a plurality of dental separators may be used simultaneously in accordance with the present invention. For example, a plurality of dental separators 40, 40' may be used to increase the interproximal spaces between a treated tooth 68 and both of its neighboring abutting teeth 70, 70' such that the tines can extend through the space defined by a yoke of a similar device.

Figure 9:
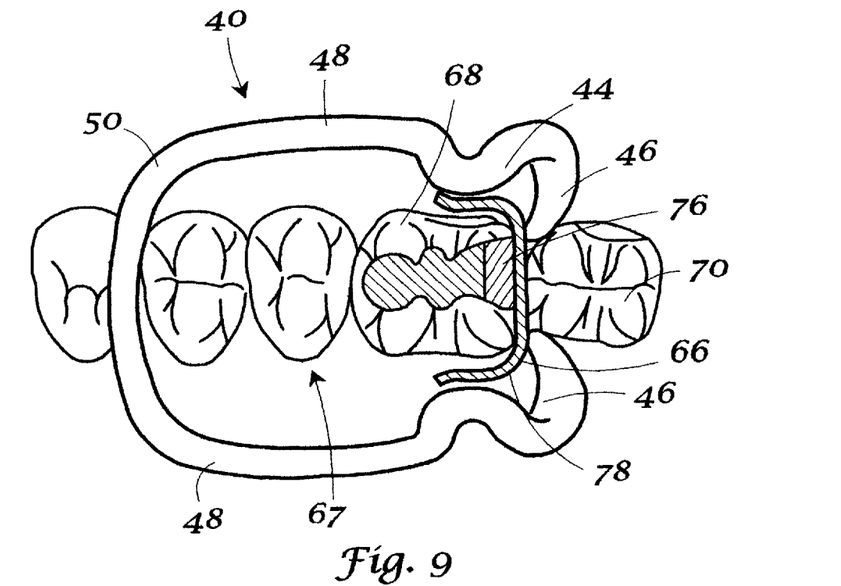
FIG. 9 is a plan view of the dental separator and matrix stabilizing device of FIG. 7 in use on a dental arch as a matrix stabilizer.

Referring to FIG. 9, when restoring a portion of a treated tooth 68 which has been damaged by decay, a dentist must remove the damaged tissue and fill the resultant void 76 with a restorative material such as silver amalgam or composite resins. To rebuild the natural contours of a proximally decayed tooth, a dentist will require a temporary form or matrix 66 to occlude part of tooth void 76 while fluid restoratives are inserted into the void, retained therein and hardened. Such matrices often require stabilization against a treated tooth by pressure on their free end flanges 78. In use, a dentist first positions matrix 66 interdentally, compresses matrix 66 to the gingival cavomargin by inserting a pressure wedge 67, next enlarges the tine-to-tine gap 60 of dental separator 40 by opening the spring yoke 42 with spreading forceps 58 to clear the bulk of involved teeth 68, 70, and then places tines 46 in such a manner to adapt the free flanges 78 of matrix 66 to the remaining tooth tissue, as shown in FIGS. 7–9. Once matrix 66 is stabilized against the treated tooth 68, the contours of matrix 66 can be modified to more accurately reproduce natural tooth anatomy and physiology.

Figure 10:
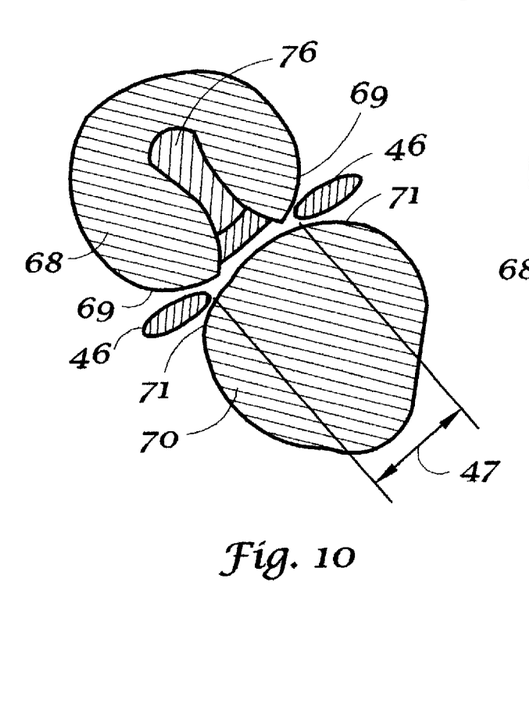
FIG. 10 is a sectional view of the dental separator and matrix stabilizing device of FIG. 1, having the cross-sectional shape shown in FIG. 3A, in use and poised to engage abutting teeth.
Figure 11:
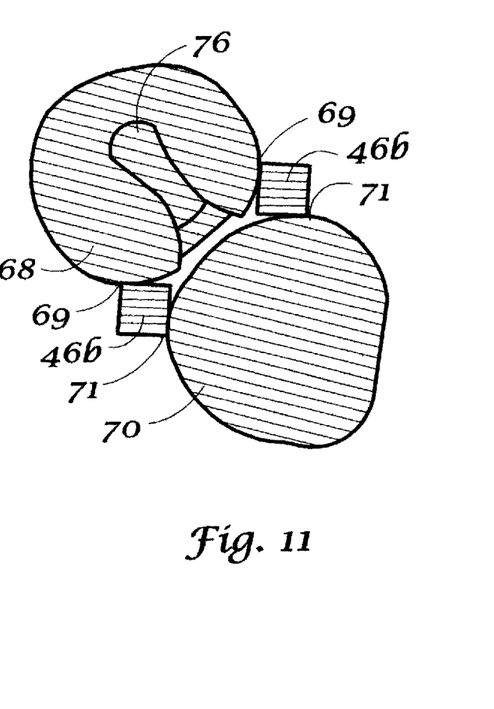
FIG. 11 is a sectional view of a modified dental separator and matrix stabilizing device similar to that shown in FIG. 10 but having the cross-sectional shape shown in FIG. 3B in use and engaging abutting teeth.

As shown in FIGS. 10 and 11, tines 46, 46b include a cross-section having a contact portion 79 that is relatively thinner than the main body portion 81. Accordingly, tines 46, 46b are shaped such that they may enter the interproximal space between involved teeth 68, 70 and contact the angled interdental surfaces 69, 71 of the teeth. Accordingly, tines 46, 46b have a tapered cross-section for engaging the interdental surfaces.

Additionally, the dental separator of the present invention may be used to carry materials such as warmed wax compounds or plastic compositions to a treatment site, to deflect a rubber dam, and to deflect gingival tissues. In the case that decay has destroyed tooth tissues at abutting zones and the involved teeth have migrated mesially to close the resulting void, the dental separator of the present invention may be used to bias the involved teeth toward their original positions.

Figure 12:
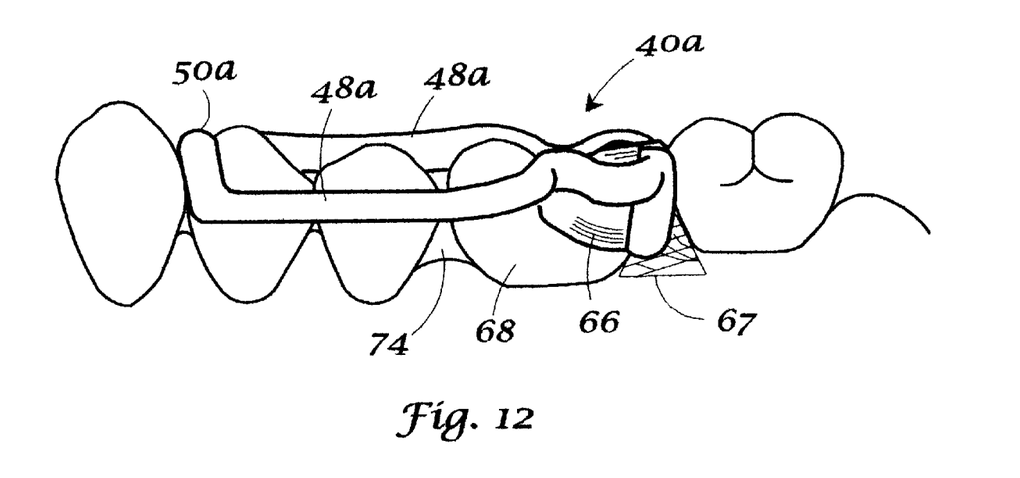
FIG. 12 is a lateral view of a modified dental separator and matrix stabilizing device similar to that shown in FIG. 7.
Figure 13:
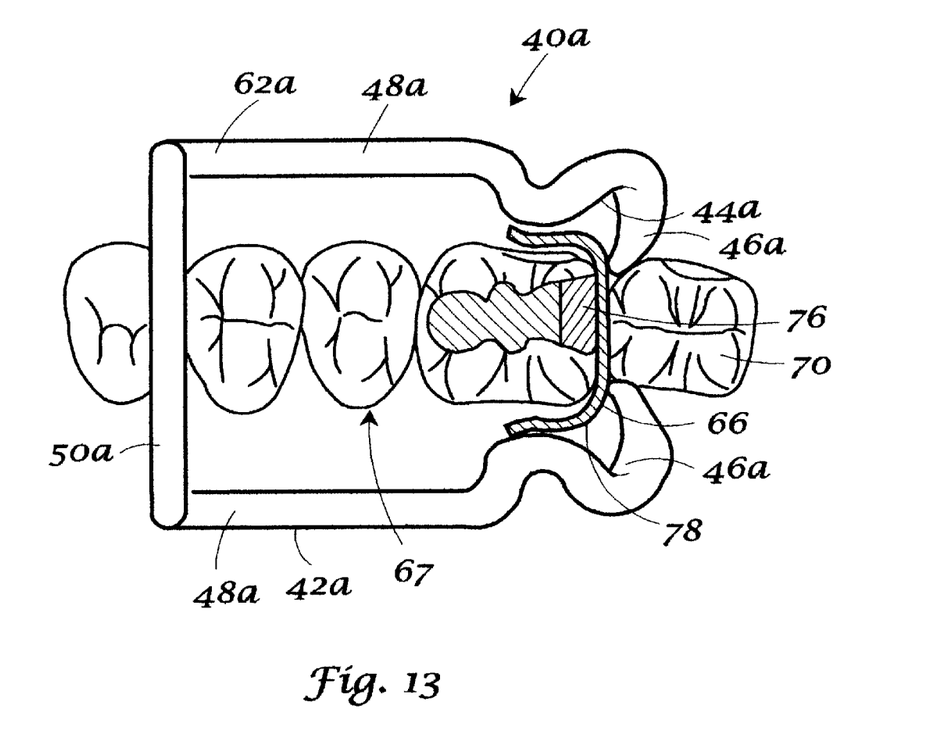
FIG. 13 is a plan view of the dental separator and matrix stabilizing device shown in FIG. 12.

The aforesaid structure is subject to wide modifications falling within the scope of the present invention. For example, FIGS. 12 and 13 shown an alternative embodiment in which dental separator 40a is more angular in shape and yoke 42a includes a steeper declining extension 62a and a straighter transverse segment 50a. This embodiment has all of the advantages as the embodiment discussed above. One should appreciate that the dental separator of the present invention may take others shapes and dimensions, as discussed below.

Figure 14:
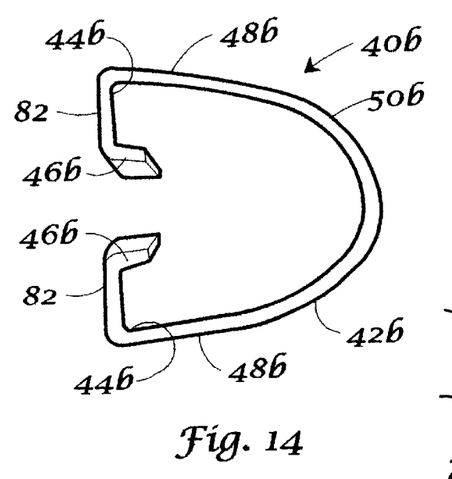
FIG. 14 is a plan view of a modified dental separator and matrix stabilizing device similar to that shown in FIG. 2.
Figure 15:
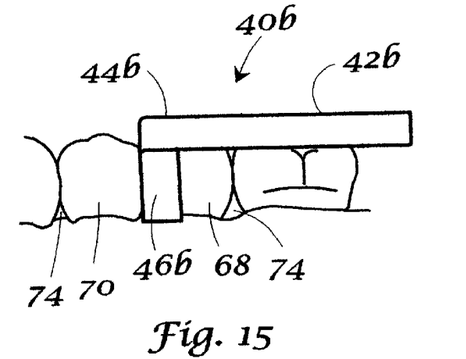
FIG. 15 is a lateral view of the dental separator and matrix stabilizing device shown in FIG. 14.

For example, FIGS. 14 and 15 show a dental separator 40b having lateral extensions 82 connecting tines 46b to longitudinal segments 48b of yoke 42b. In this embodiment, a corner formed by lateral extensions 82 and longitudinal segments 48b serves as engagement receptacle 44b.

Figure 16:
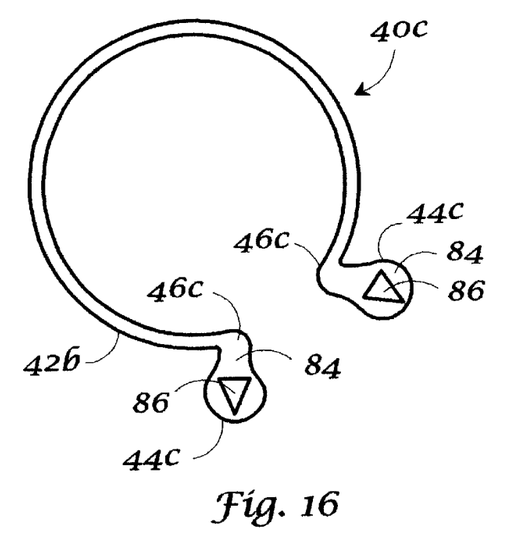
FIG. 16 is a plan view of a modified dental separator and matrix stabilizing device similar to that shown in FIG. 2.
Figure 17:
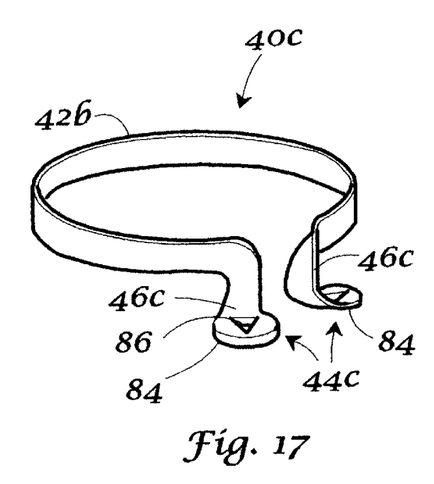
FIG. 17 is a lateral view of the dental separator and matrix stabilizing device shown in FIG. 16.

FIGS. 16 and 17 show a dental separator 40c having engagement receptacles 44c in the form of engagement flanges 84 having apertures 86 for receiving teats 56 of spreading forceps 58 (FIG. 4). Unlike the embodiments discussed above, engagement receptacles 44c are not located at yoke ends 52c. Instead, an engagement flange 84 of each engagement receptacle 44c extends from a lower edge of tine 46c. Also shown in FIGS. 16 and 17, yoke 42c is circular in shape.

Figure 18:
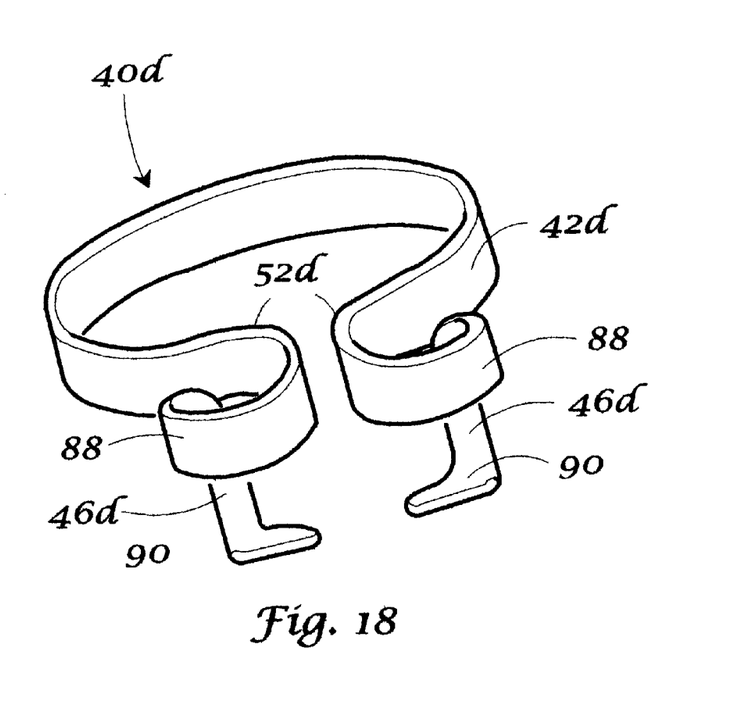
FIG. 18 is a plan view of a modified dental separator and matrix stabilizing device similar to that shown in FIG. 2.
Figure 19:
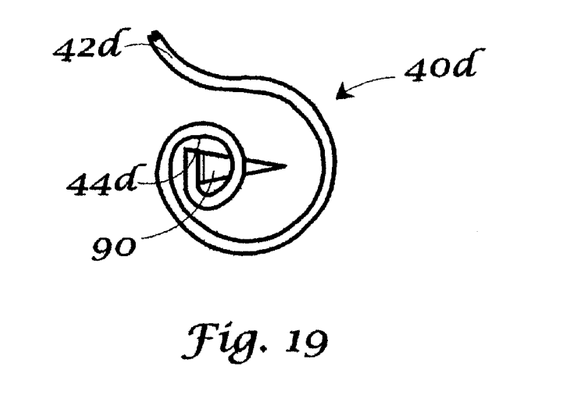
FIG. 19 is a lateral view of the dental separator and matrix stabilizing device shown in FIG. 18.

FIGS. 18 and 19 show a modified dental separator 40d in which engagement receptacles 44d are formed by circular engagement loops 88. Loops 88 extend from yoke ends 52d with a curvature which is reversed from that of circular yoke 42d. Tines 46c extend downwardly from respective termini of loops 88 at a slightly acute angle with respect to the yoke plane in a manner similar to that discussed above. Opposing triangular wedges 90 extend from lower ends of tines 46d toward one another for contacting the interproximal spaces of involved teeth.

Figure 20:
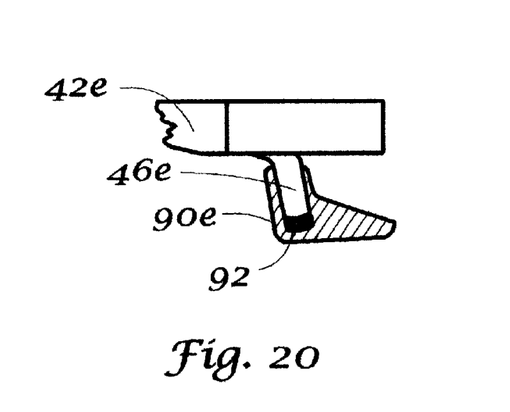
FIG. 20 is a lateral view of a modified dental separator and matrix stabilizing device similar to that shown in FIG. 19.

FIG. 20 shows a modified dental separator 40e similar to that of FIGS. 18 and 19 in which separating wedges 90e are formed separately of tines 46e. In particular, separating wedges 90e are discrete from tines 46e. Separating wedges 90e may be molded of various materials that will not adhere to restorative chemicals used in a dental procedure, such as high-density polyethylene and other suitable plastics and elastomers. Such molded separating wedges 90e may include an indentation therein for receiving lower ends of tines 46e. Tines 46e may be threadably engaged with wedges 90 or connected thereto with other suitable means such as an adhesive.

Many of the elements of the modifications of FIGS. 2–10 resemble those of the preceding modifications and the same reference numerals followed by the subscripts a, b, c, d and e, respectively, indicate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A dental separator for forcing adjacent teeth of a dental arch apart from one other for use with a spreading instrument, said dental separator comprising:

a spring yoke having first and second ends;

first and second opposing tines adapted for wedging between and against interdental surfaces of the adjacent teeth and forcing the teeth apart, each said first and second tine connected to said first and second end of said yoke and extending downwardly therefrom, respectively, said spring yoke being formed to bias said first and said second opposing tines toward each other along a closure path to generate a force vector substantially perpendicular to said closure path and force the adjacent teeth apart, and first and second instrument engagement structures adapted for cooperation with the spreading instrument to separate said tines for placement between adjacent teeth, respectively, each said first and second instrument engagement structures being located proximal said first and second opposing tines, respectively.

2. A dental separator according to claim 1 wherein said opposing tines, said engagement structures, and said spring yoke are integral.

3. A dental separator according to claim 1 wherein said dental separator is metal and is monolithically formed.

4. A dental separator according to claim 1 wherein said opposing tines have a shape adapted to engage the profile of a tooth along a zone of contact extending along a length of said tines.

5. A dental separator according to claim 4 wherein said opposing tines have a substantially concave profile with respect to one another, said concave profile extending substantially parallel to said yoke.

6. A dental separator according to claim 1 wherein said tines have a cross-section including a contact portion thinner than a main body portion, said contact portion adapted to engage the interdental surfaces of the adjacent teeth.

7. A dental separator according to claim 1 wherein said tines have a tapered cross-section adapted to engage the interdental surfaces of the adjacent teeth.

8. A dental separator according to claim 1 wherein said yoke comprises a declining extension whereby said longitudinal segments of said yoke extend below the occlusal plane of the dental arch.

9. A dental separator according to claim 1 wherein said longitudinal segments are spaced apart a first distance, said tines are spaced apart a second distance less than said first distance whereby said tines of said dental separator are adapted to extend between longitudinal segments of a second, identical dental separator.

10. A dental separator according to claim 1 wherein said spring yoke comprises:

a semicircular segment; and first and second straight segments located between said semicircular segment and said first and second ends of said spring yoke, respectively.

11. A dental separator according to claim 1 wherein said longitudinal segments extend within a yoke plane, each said tine extending downwardly from said yoke at an acute angle with respect to said yoke plane.

12. A dental separator for forcing adjacent teeth of a dental arch apart from one other for use with a spreading instrument, said dental separator comprising:

a spring yoke having first and second ends;

first and second opposing tines adapted for wedging between and against interdental surfaces of the adjacent teeth and forcing the teeth apart, each said first and second tine connected to said first and second end of said yoke and extending downwardly therefrom, respectively, said spring yoke being formed to bias said first and said second opposing tines toward each other along a closure path to generate a force vector substantially perpendicular to said closure path and force the adjacent teeth apart, and first and second instrument engagement structures adapted for cooperation with the spreading instrument to separate said tines for placement between adjacent teeth, respectively, each said first and second instrument engagement structures being located proximal said first and second opposing tines, respectively, further comprising first and second engagement flanges located proximate said first and second tines, respectively; and first and second aperttures extending through said first and second engagement flanges, respectively, wherein said first and second apertures form said first and second engagement structures, repectively.

13. A dental separator according to claim 1 wherein said spring yoke further comprises first and second loops proximate said first and second ends, said loops forming said first and second structures, respectively.

14. A dental separator according to claim 1 wherein each said first and second tine is wedge shaped.

15. A dental separator according to claim 14 wherein said first and second tines further comprise first and second molded wedges, respectively.

16. A dental separator according to claim 15 wherein each said first and second molded wedges is an elastomer or a plastic.

17. A dental separator for forcing adjacent teeth of a dental arch apart from one other for use with spreading forceps having first and second teats, said dental separator comprising:

a resilient material having an elliptical, rectangular, triangular or circular cross section;

a spring yoke formed of said resilient material having first and second ends, each said fist and second end extending within a yoke plane;

first and second opposing tines adapted for wedging between and against interdental surfaces of the adjacent teeth and forcing the adjacent teeth apart each said first and second tine extending from said first and second ends of said yoke, repectively, at an angle from said yoke plane, whereby said spring yoke biases said first and second tines toward each other along a closure path; and first and second structures adapted for engaging first and second teats of the spreading forceps, respectively, each said first and second receptacle located proximal said first and second opposing tines, respectively, and within said yoke plane.

18. A dental separator according to claim 17 wherein said angle is approximately 70–90°.

* * * * *